United States Patent
Nobutani et al.

(10) Patent No.: US 8,079,363 B2
(45) Date of Patent: Dec. 20, 2011

(54) INHALER

(75) Inventors: Toshiyuki Nobutani, Yokohama (JP); Yoshinari Ikegami, Kawagoe (JP)

(73) Assignee: Canon Kabushiki Kaisha, Tokyo (JP)

( * ) Notice: Subject to any disclaimer, the term of this patent is extended or adjusted under 35 U.S.C. 154(b) by 1029 days.

(21) Appl. No.: 11/911,626

(22) PCT Filed: Apr. 18, 2006

(86) PCT No.: PCT/JP2006/308501
§ 371 (c)(1),
(2), (4) Date: Oct. 15, 2007

(87) PCT Pub. No.: WO2006/118064
PCT Pub. Date: Nov. 9, 2006

(65) Prior Publication Data
US 2008/0190422 A1    Aug. 14, 2008

(30) Foreign Application Priority Data

Apr. 27, 2005  (JP) .................................. 2005-129059

(51) Int. Cl.
*A61M 11/00* (2006.01)
*A61M 15/00* (2006.01)
*F16K 31/02* (2006.01)

(52) U.S. Cl. ......... 128/200.24; 128/200.14; 128/200.16; 128/203.12; 128/203.15; 128/203.21; 128/204.23

(58) Field of Classification Search ............. 128/200.14, 128/200.16, 203.12, 203.15, 203.21, 204.23
See application file for complete search history.

(56) References Cited

U.S. PATENT DOCUMENTS

| | | | |
|---|---|---|---|
| 5,487,378 A * | 1/1996 | Robertson et al. ........ | 128/200.16 |
| 6,547,357 B1 | 4/2003 | Tsuruoka ........................ | 347/14 |
| 6,652,057 B2 | 11/2003 | Masuda et al. .................. | 347/14 |
| 7,008,035 B2 | 3/2006 | Masuda et al. .................. | 347/19 |
| 2007/0062520 A1 | 3/2007 | Nobutani et al. ........ | 128/200.14 |

(Continued)

FOREIGN PATENT DOCUMENTS

JP            57-87371 A    5/1982

(Continued)

OTHER PUBLICATIONS

PCT International Search Report mailed Jul. 12, 2006, for International Application No. PCT/JP2006/308501.

(Continued)

*Primary Examiner* — Patricia Bianco
*Assistant Examiner* — Nihir Patel
(74) *Attorney, Agent, or Firm* — Fitzpatrick, Cella, Harper & Scinto

(57) ABSTRACT

An inhaler and a direct current power supply voltage control device with a relatively simple structure that output a predetermined drive voltage according to a specified time interval to a drive object such as a heating resistor. An inhaler 1 is equipped with a liquid ejection head 9, and is set so that a user is able to inhale liquid droplets ejected from the liquid ejection head 9. The inhaler 1 includes: specifying means 4, 5 and 6 for specifying a drive voltage 701 based on preset voltage data 501 respectively corresponding to preset time intervals that respectively specify the drive voltage 701 of the liquid ejection head 9 in synchronization with the start of control of a drive signal 302 of the liquid ejection head 9; and drive means 3 and 7 for driving the liquid ejection head 9 according to the drive signal 302 at the specified drive voltage 701.

3 Claims, 8 Drawing Sheets

U.S. PATENT DOCUMENTS

2007/0227534 A1    10/2007    Nobutani et al. ........ 128/200.14
2007/0240706 A1    10/2007    Kobayashi et al. ...... 128/200.14

FOREIGN PATENT DOCUMENTS

| JP | 06-079905 A | 3/1994 |
| JP | 11-64462 | 3/1999 |
| JP | 11-240148 | 9/1999 |
| JP | 2003-211671 | 7/2003 |
| JP | 2004-97617 A | 4/2004 |

OTHER PUBLICATIONS

Office Action mailed May 6, 2011 by the Japanese Patent Office in counterpart Japanese patent application No. 2005-129059, with concise statement of relevance in English (above).

* cited by examiner

US 8,079,363 B2

INHALER

TECHNICAL FIELD

The present invention relates to an inhaler and a direct current power supply voltage regulation or control device, and particularly, to an inhaler for ejecting a liquid such as a drug as droplets to be inhaled by users, and a direct current power supply voltage regulation or control device usable in such an inhaler or the like.

BACKGROUND ART

Conventionally, as a technique for ejecting microdroplets, a technique regarding head drive voltage control for an ink jet printer has been reported (refer to Japanese Patent Application Laid-Open No. 2003-211671 and No. H11-240148). In addition, as a technique for a direct current power supply device, a technique regarding a battery simulator for referring to set and recorded characteristics to control output voltage has been reported (refer to Japanese Patent Application Laid-Open No. H11-064462).

DISCLOSURE OF THE INVENTION

However, as disclosed in the above-mentioned Japanese Patent Application Laid-Open No. 2003-211671, in voltage adjustment by the number of simultaneously ejecting nozzles used in head drive voltage control circuits of conventional ink jet printers, when an inhaler is set so that the number of simultaneously ejecting nozzles is always at maximum, only a constant voltage could be set at all times. In addition, even with a voltage adjustment method by detecting temperature rises of the head disclosed in Japanese Patent Application Laid-Open No. 11-240148, or a method for storing drive voltage data disclosed in the same Application Laid-Open No. 11-240148, when selection means for the drive voltage data is restricted to just those based on head temperature, the adjustment will be relatively gradual by means of temperature-detecting resistors or diodes.

On the other hand, as in the case of Japanese Patent Application Laid-Open No. H11-064462, a system involving referring to and computing battery internal characteristics set and recorded by load fluctuation to control an output voltage will require load fluctuation detection means and a computing function even if the system has a setting and recording function. Therefore, there was a problem that it was difficult to install them to small portable devices, such as an inhaler, which are incapable of directly specifying drive voltage using only predetermined characteristics.

In consideration of the above problems, the inhaler according to the present invention is an inhaler for use in a user's inhalation of a liquid, and may comprise a liquid ejection head for ejecting a liquid, and a drive unit for reading a voltage data from a plurality of preset voltage data respectively corresponding to preset time intervals, and driving the liquid ejection head at a drive voltage specified based on the read voltage data.

As an embodiment of the present invention, the present inhaler is characterized in that the switching means includes: a specifying means for specifying a drive voltage on a basis of preset voltage data respectively corresponding to preset time intervals (which are time obtained by continuously segmenting a drive period from the beginning thereof by a predetermined length; in the present specification, and the time intervals may also be referred to as time or period) that respectively specify a drive voltage of the liquid ejection head in synchronization with the start of control of a drive signal of the liquid ejection head; and drive means for driving the liquid ejection head according to the drive signal at the specified drive voltage. More specifically, as shown in FIG. 2, the specifying means includes: a time control circuit for controlling time intervals that specify a drive voltage of the liquid ejection head in synchronization with the start of control of a drive pulse signal of the liquid ejection head; a voltage table for recording a drive voltage corresponding to each time interval as voltage data; and a drive voltage specifying circuit for specifying a drive voltage by reading voltage data from the voltage table; and the drive means includes: a drive pulse control circuit for controlling a drive pulse signal of the liquid ejection head; and a drive voltage control circuit for outputting at the specified drive voltage. According to such inhalers, the drive voltage can be outputted according to the voltage data recorded in the voltage table and the specified time intervals while the drive pulse control circuit is generating drive pulse signals for driving the liquid ejection head to perform liquid ejection.

In another embodiment, the switching means is means for changing a drive period and/or drive pulse width of the liquid ejection head with elapse of the drive time.

Additionally, in consideration of the above problems, the direct current power supply voltage control device according to the present invention is characterized by including: a specifying means for specifying a drive voltage on a basis of preset voltage data respectively corresponding to preset time intervals that respectively specify a drive voltage of a drive object in synchronization with the start of control of a drive signal for the drive object; and a drive means for controlling a voltage from the direct current power supply to generate the specified drive voltage, and driving the drive object according to the drive signal at the drive voltage.

According to the present invention, the ejection conditions of a liquid ejection head can be controlled with good precision although it has a relatively simple configuration. For instance, in an inhaler that ejects a nearly constant amount of liquid droplets in a relatively short time according to inhalation by a user, since drive voltage to be outputted can be estimated with relatively high precision with the time from the beginning of driving, drive voltage control of the liquid ejection head can be performed with a high speed and a high precision by voltage predetermined according to each time interval during driving, even in relatively small portable devices. Also, in direct current power supply voltage control device that controls a voltage from a general direct current power supply to output to a drive object, predetermined voltage can be outputted with a relatively simple configuration according to time intervals that respectively specify drive voltages.

Other features and advantages of the present invention will be apparent from the following description taken in conjunction with the accompanying drawings, in which like reference characters designate the same or similar parts throughout the figures thereof.

BEST MODE FOR CARRYING OUT THE INVENTION

Preferred embodiments of the present invention will now be described in detail in accordance with the accompanying drawings.

The inhaler according to the present invention is an inhaler for use in a user's inhalation of a liquid, and the inhaler including: a liquid ejection head for ejecting a liquid; a drive unit for driving the liquid ejection head; and switching means for switching the drive conditions of the drive unit with elapse of a drive time of the drive unit.

Example of configurations for the switching means include a configuration where the switching means is used as means for changing the drive voltage of the liquid ejection head with elapse of the drive time, and a configuration where the switching means is used as means for changing the drive periods of the liquid ejection head with elapse of the drive time.

Embodiments for carrying out the present invention will now be described with reference to the attached drawings.

Incidentally, in the embodiments described below, an inhaler equipped with a liquid ejection head having a structure of a heating resistor will be explained as an example. However, the present invention is not limited to this embodiment, and conventional and known spray devices such as a system for spraying droplets by means of vibration of a piezoelectric element, or atomization means through generation of ultrasonic waves can be used.

First Embodiment

As a first embodiment, a specific example of a configuration where the switching means is means for changing the drive voltage of a liquid ejection head with elapse of its drive time will now be explained using the drawings.

Figure 1:
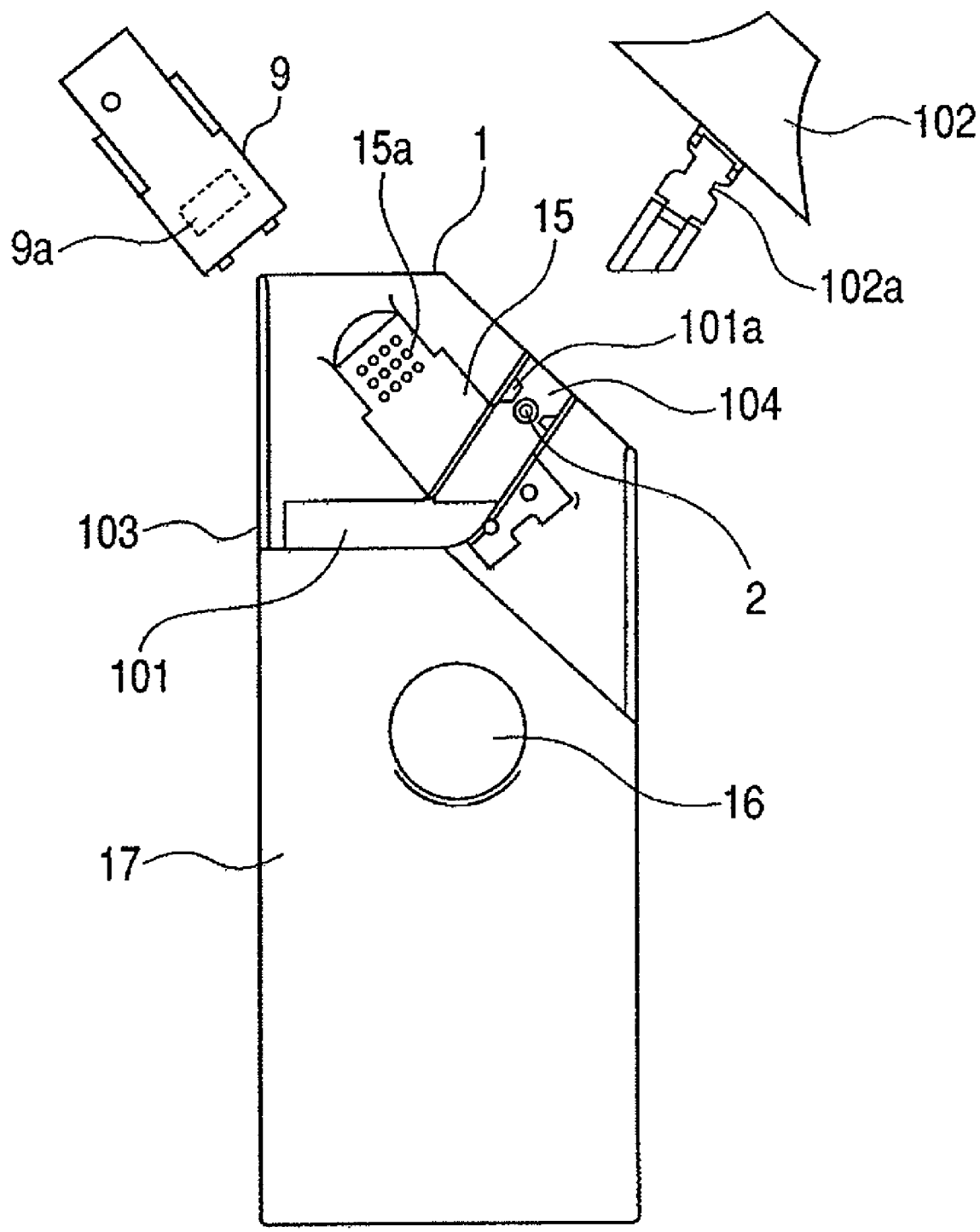
FIG. 1 is an external view of an example of an inhaler.

FIG. 1 is an external view of an embodiment of an inhaler. In FIG. 1, reference numeral 1 denotes an inhaler, 9 denotes a detachable liquid ejection head storing a liquid to be ejected, 101 denotes a flow path provided inside the inhaler 1, and 102 denotes a detachable mouthpiece that is used by a user upon inhalation. The liquid ejection head 9 has a tank storing the liquid, and an ejection section 9a (exposed to the opposite face of the paper) for ejecting a liquid. The liquid ejection head 9 is detachably mounted to a liquid ejection head mounting section 15 provided on the side of the inhaler 1. In addition, when the liquid ejection head 9 is mounted to the liquid ejection head mounting section 15, its electric connection section connects to an electric contact 15a of the ejection head mounting section 15 and receives an electric power and various electric control signals from a battery and control circuits on the side of the inhaler 1.

The mouthpiece 102 is also detachably mounted to the inhaler 1 so that its recessed portion 102a engages a protruded portion 101a provided in the gas flow path 101. From a hygiene standpoint, since it is desirable for the liquid ejection head 9 and the mouthpiece 102 to be either disposable or regularly replaced, they are formed separately from the inhaler 1. However, they may be integrally formed with the inhaler as well.

In addition, reference numerals 103 and 104 respectively denote an inlet (air intake) and an outlet (exhaust) of the flow path 101, while 2 denotes inhalation detection means placed inside the flow path 101. When the inhalation detection means 2 detects inhalation as the user performs an inhalation action, the inhaler 1 drives the ejection section 9a of the liquid ejection head 9. Liquid ejected from the liquid ejection head 9 and converted into droplets by the driving is directed from the inlet 103 side through the flow path 101 to the outlet 104 by an airflow generated by the inhalation, and is inhaled by the user via the mouthpiece 102 mounted to the outlet 104. In the example shown in the figure, although the gas flow path 101 is formed to be crooked in consideration of placement in relation to the other components, it can also be configured to be straight. Furthermore, when the liquid ejection head 9 is mounted to the liquid ejection head mounting section 15, its ejection section 9a is exposed to the gas flow path 101.

Moreover, reference numeral 16 denotes a power button, while 17 denotes a sliding cover. Pressing the power button 16 performs inhalation action. When inhalation is initiated by the user, and a negative pressure (related to an inhalation speed or flow rate) detected by the inhalation detection means 2 such as a pressure sensor reaches a liquid-ejectable region, liquid ejection is initiated from the ejection section 9a of the liquid ejection head 9 under control by the control circuit. The cover 17 is slid and closed to seal an opened section of the upper face of the gas flow path 101, thereby fixing the liquid ejection head 9. FIG. 1 depicts an opened state. A power switch 16 may be activated in conjunction with the closing of the cover 17.

Figure 2:
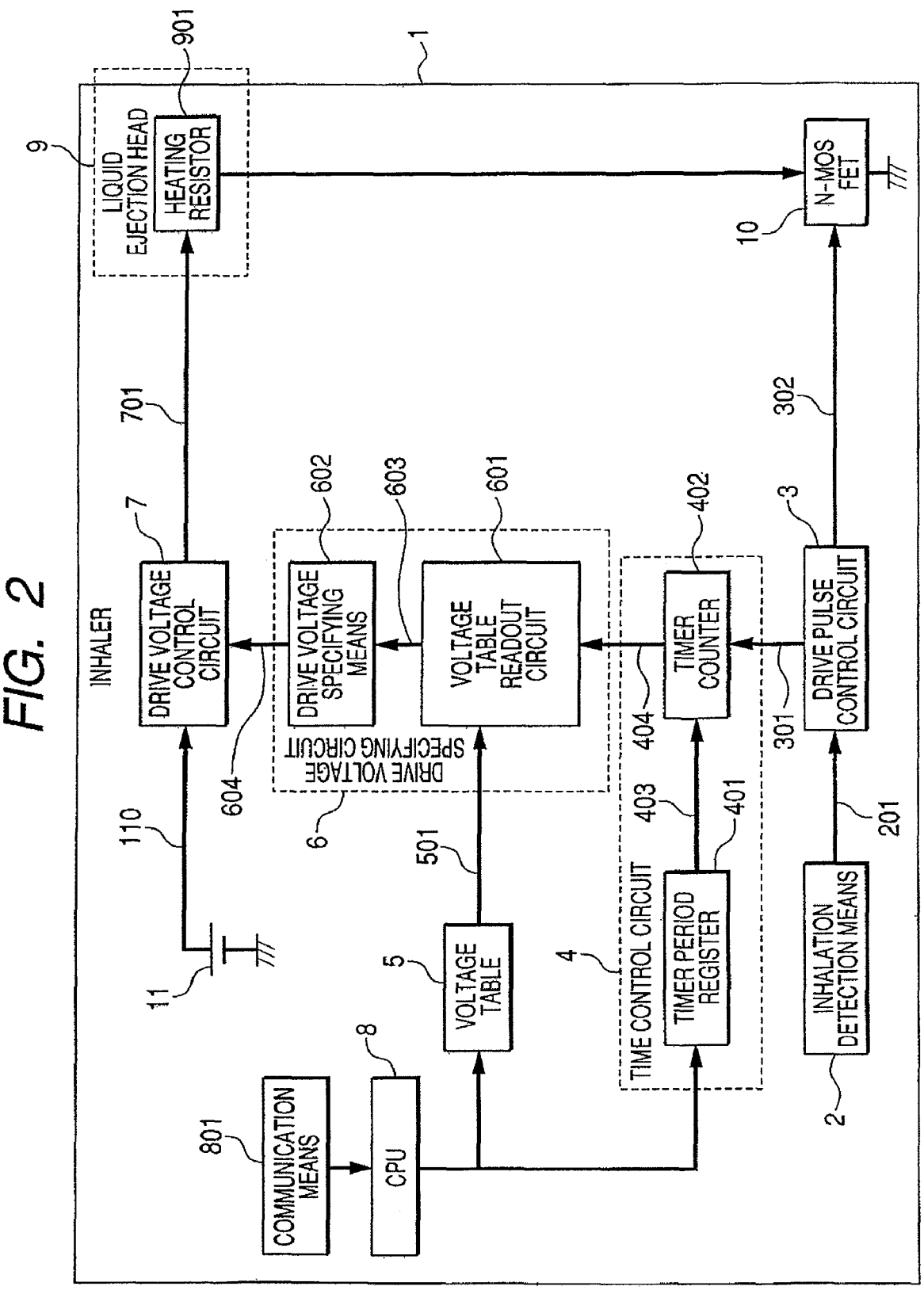
FIG. 2 is a circuit configuration diagram of an inhaler according to a first embodiment of the present invention.

FIG. 2 is a circuit configuration diagram of the inhaler of the present embodiment. In FIG. 2, reference numeral 3 denotes a drive pulse control circuit, 4 denotes a time control circuit, 5 denotes a voltage table, 6 denotes a drive voltage specifying circuit, 7 denotes a drive voltage control circuit, 8 denotes a CPU, 10 denotes an N-MOS field effect transistor, 11 denotes a direct current power supply (e.g., battery or the like), 801 denotes communication means connected to an external computer not shown, and 901 denotes a heating resistor integrally configured inside the liquid ejection head 9.

In the above configuration, when the inhalation detection means 2 detects inhalation by a user via the mouthpiece 102, the inhalation detection means 2 notifies the drive pulse control circuit 3 using an inhalation detection signal 201, and instructs drive initiation.

Upon receiving instructions for drive initiation, the drive pulse control circuit 3 instructs the time control circuit 4 to initiate time control using a drive initiation timing signal 301. Incidentally, the drive initiation timing signal 301 is a signal with a logical level that becomes true upon receiving the drive initiation instruction, and remains true until drive termination.

The time control circuit 4 is composed of a timer period register 401 and a timer counter 402. Upon receiving instructions for time control initiation from the drive control circuit 2 using the drive initiation timing signal 301, the timer counter 402 generates a table readout timing signal 404 for each period indicated by period setting data 403 retained in the timer period register 401. An instruction for reading the voltage table 5 is sent to the drive voltage specifying circuit 6.

The drive voltage specifying circuit 6 is composed of a voltage table readout circuit 601 and drive voltage specifying means 602. The voltage table readout circuit 601 sequentially reads voltage data from the voltage table 5 for each table readout timing signal 404, and instructs the drive voltage specifying means 602 in the form of a voltage setting signal 603. The drive voltage specifying means 602 adjusts a drive voltage specifying signal 604 based on the voltage setting signal 603, and specifies a drive voltage 701, which is an output of the drive voltage control circuit 7.

The drive voltage control circuit 7 is a DC-DC converter connected as a power supply voltage 110 to a positive voltage terminal of the direct current power supply 11, and controls the drive voltage 701 to be the voltage indicated by the drive voltage specifying signal 604.

The drive voltage 701 is connected to a positive voltage terminal of a heating resistor 901 inside the liquid ejection head 9. A negative voltage terminal of the heating resistor 901 inside the liquid ejection head 9 is connected to a drain terminal of the N-MOS field effect transistor 10. In addition, a source terminal of the N-MOS field effect transistor 10 is connected to a negative voltage terminal (GND) of the direct current power supply 11, and a drive pulse signal 302 is connected to a gate terminal of the N-MOS field effect transistor 10.

Meanwhile, the drive pulse control circuit 3 instructs voltage control initiation using the drive initiation timing signal 301, and at the same time generates a drive pulse signal 302 to initiate the driving of the liquid ejection head 9. Therefore, when the drive pulse signal 302 outputs a voltage (high level) that is larger than a gate-source cutoff voltage of the N-MOS field effect transistor 10, a current according to the voltage between the drive voltage 701 and the GND is applied to the heating resistor 901, and continues to be applied throughout the high level period of the drive pulse signal 302. The liquid ejection head 9 ejects droplets in this manner.

Period setting data 403 retained in the aforementioned timer period register 401 is an 8-bit width binary data, and may take any value between 0 and 255. In addition, the timer counter 402 is a 19-bit width binary counter that counts values between 0 and 524287, and clears the counter value to 0 when the count value (N) takes the value indicated by the following formula (1) specified by the period setting data 403 (X). At the same time, table readout timing signals 404 are generated during a single count, and count operation is repeatedly continued as long as time control is instructed by the drive initiation timing signal 301.

$$N = (X+1) \times 1440 - 1 \quad \text{Formula (1)}$$

The frequency (FMCK) of a reference clock (MCK) necessary for operation of the entire electronic circuitry of the inhaler 1 is 36.864 MHz. The reference clock is used as an operation clock for the timer counter 402. Therefore, the period of the table readout timing signal 404 actually generated by the timer counter 402 is obtained by adding 1 to the count value obtained by the above Formula (1), and then dividing the result by the reference clock frequency (refer to Formula (2) below). Thus, it is possible to specify the period of the table readout timing signal 404 in units of 39.0625 μs in the range of 39.0625 μs to 10 ms.

$$T = (N+1) \div FMCK \quad \text{Formula (2)}$$

The voltage table 5 is a storage device that retains 512 voltage data 501 having 8-bit width. After receiving instructions for voltage control initiation, the voltage table readout circuit 601 performs sequential reading of voltage data 501 from the voltage table 5, always starting with the first voltage data 501. From the above formulas (1) and (2), as well as 512, which is the number of voltage data 501 of the voltage table 5, it is found that the drive voltage 701 can be controlled over a maximum period of 5.12 seconds.

On the other hand, the voltage table 5 and the timer period register 401 is connected to the CPU 8, and are in turn connected via the communication means 801 to an external computer not shown. Therefore, the external computer can set the voltage data 501 and period setting data 403, which are their respective set values.

Figure 8:
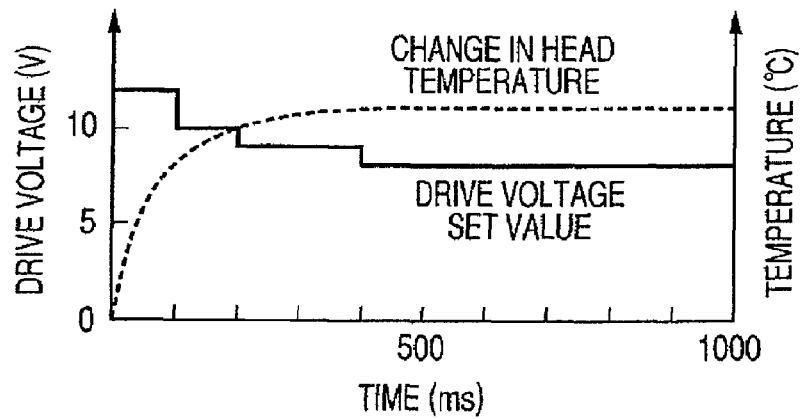
FIG. 8 is a graph for depicting current control of the head by drive pulse signals, when drive voltages are specified to differently set values for each continuous time interval (time, period)

Thus, preset voltage is sequentially specified from drive initiation for each similarly preset period (time interval), and under control of the drive voltage 701 based thereon, a current is applied to the heating resistor 901 according to the drive pulse signal 302, resulting in ejection of liquid droplets from the liquid ejection head 9. FIG. 8 depicts current control by drive pulse signals, where drive voltage is specified to each set value at each time interval. It can be seen that drive voltage control is performed so that the head temperature first rises gradually from drive initiation, and then maintains a substantially constant value.

In this manner, it is possible to perform the driving of the liquid ejection head by setting the time intervals that specify the voltage data and drive voltage based on the temperature rise characteristics of the structure of the liquid ejection head and the liquid around its ejection orifice, and the temporal change characteristics of the drive voltage necessary to eject liquid droplets, due to driving of the heating resistor. According to such an inhaler, the setting of the drive voltage and time intervals according to the characteristics of the liquid ejection head eliminates the need to apply excessive cooling measures to the liquid ejection head, and thereby allows simplification of the liquid ejection head structure to enable its production at a low cost.

As seen from the present embodiment (as well as the embodiments described below), according to an inhaler having specifying means including: a time control circuit for controlling time intervals for specifying the drive voltage of the liquid ejection head in synchronization with control start of the drive pulse signal of the liquid ejection head; a voltage table for recording a drive voltage corresponding to each time interval as voltage data; and a drive voltage specifying circuit for reading the voltage data from the voltage table and specifying the drive voltage, and the drive means including: a drive pulse control circuit for controlling the drive pulse signals of the liquid ejection head; and a drive voltage control circuit that performs output at the specified drive voltage, the drive voltage can be outputted according to voltage data recorded in the voltage table and the specified time interval while the drive pulse control circuit is generating drive pulse signals and drives the liquid ejection head to perform ejection of liquid droplets.

In addition, as seen from the present embodiment (as well as the embodiments described below), by setting the time for specifying drive voltage and the voltage data to be rewritable, and by including a CPU and communication means, the time intervals for specifying the drive voltage and the voltage data can be rewritten from an external apparatus through the communication means controlled by the CPU. Moreover, according to this configuration, since the drive voltage and time intervals to be specified can be respectively set for each individual inhaler by the communication means, individual differences in control circuit characteristics due to the production conditions of the inhalers may be corrected. Furthermore, when using liquid ejection heads with different characteristics for individual inhalers A and B, it is possible to set a drive voltage and time intervals according to the characteristics of each liquid ejection head.

Although the liquid ejection head can have a structure with a ceramic piezoelectric element, as seen from the present embodiment (as well as the embodiments described below), the present invention is more effective when the structure of the liquid ejection head is a structure having a heating resistor that ejects droplets by heating due to application of a direct current. This is because, although in such an inhaler, heat accumulation is likely to occur during driving since the load to be driven is a heating resistor, it is possible to reduce the drive voltage to prevent the burning of the heating resistor surface and the burn-through of wiring conductors due to overheating and heat accumulation while maintaining the supply of power necessary for bubbling, and at the same time to reduce heat releasing parts and structures from the liquid ejection head.

Figure 3:
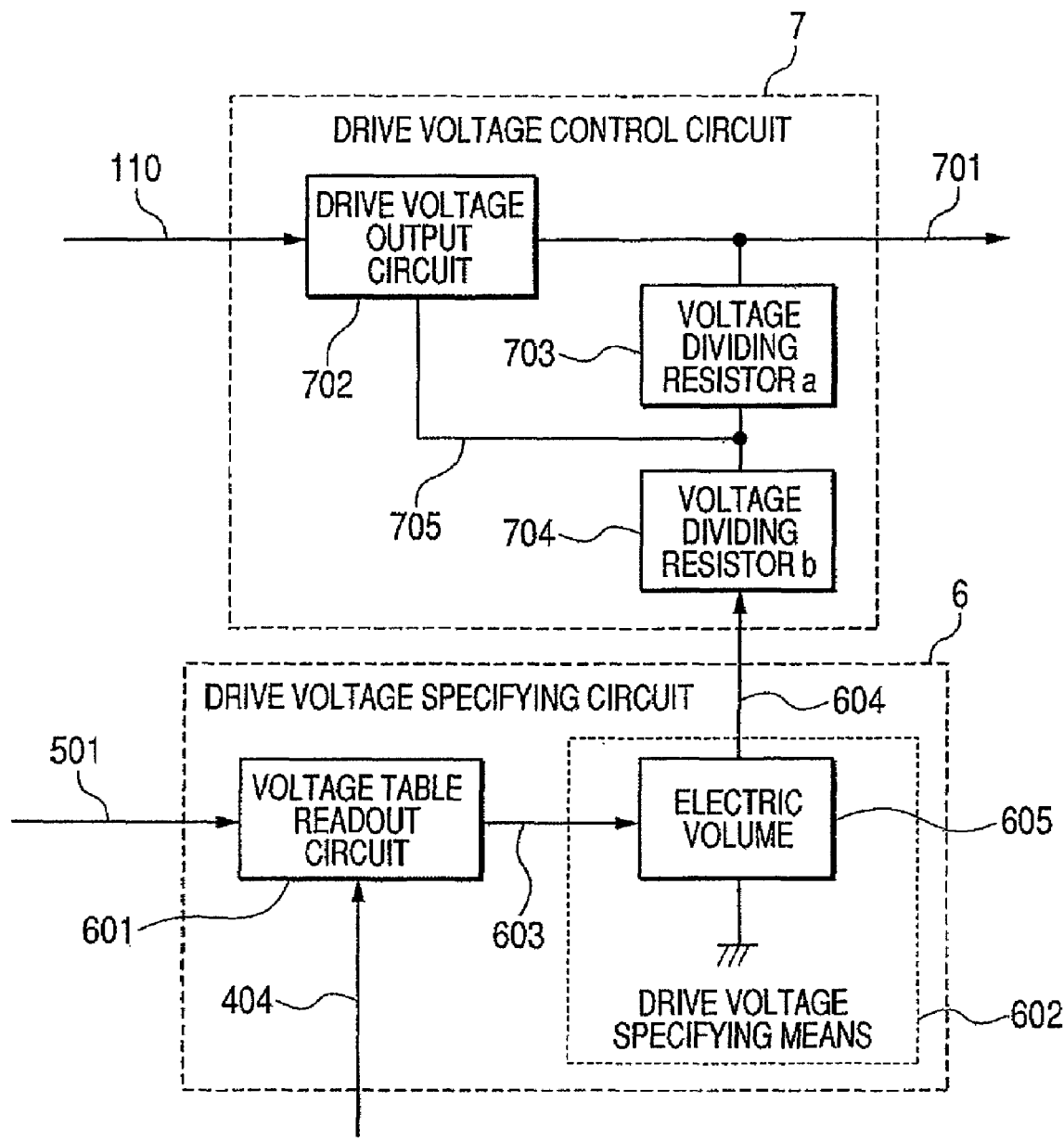
FIG. 3 is a circuit configuration diagram for explaining an example of voltage specifying means.

FIG. 3 is a circuit configuration diagram for explaining an example of the voltage specifying means 602 of the drive voltage specifying circuit 6. In FIG. 3, the drive voltage specifying means 602 is composed of an electronic volume 605. The electronic volume 605 adjusts output resistance values based on a voltage specifying signal 603. The negative voltage terminal of an output resistance of the electronic volume 605 is connected to the GND, while its other terminal, the positive voltage terminal, is connected to the drive voltage control circuit 7 as a drive voltage specifying signal 604.

The drive voltage control circuit 7 is composed of a drive voltage output circuit 702, a voltage dividing resistor a 703 and a voltage dividing resistor b 704. Upon receiving input of the power supply voltage 110, a drive voltage 701 is outputted from the drive voltage output circuit 702. Meanwhile, the voltage dividing resistor a 703 is arranged between the drive voltage 701 and the drive voltage specifying signal 604 and connected to the side of the drive voltage 701, and the voltage dividing resistor b 604 is connected in series to the side of the drive voltage specifying signal 604. A feedback voltage 705 is connected to the drive voltage output circuit 702 from the connection points of the voltage dividing resistors a and b, 703 and 704. According to this configuration, the ratio of the voltage dividing resistances can be changed by adjusting the output resistance value of the electronic volume 605 using the voltage specifying signal 603, and the drive voltage 701 may be adjusted by changing the voltage ratio of the drive voltage 701 and the feedback voltage 705.

As described above, the present example has a structure for deriving feedback voltage from a voltage dividing point obtained by resistance-dividing between a drive voltage and a reference voltage (typically, GND) to perform voltage adjustment. Although the drive voltage control circuit may have no output voltage feedback means, an inhaler is suitable to have a structure for taking a feedback voltage from a voltage dividing point obtained by resistance-dividing between the drive voltage and the reference voltage. This is because the addition of a relatively simple component such as an electronic volume to a generally used direct current power supply output circuit enables control of a drive voltage to a specified value during output of the drive voltage.

Figure 4:
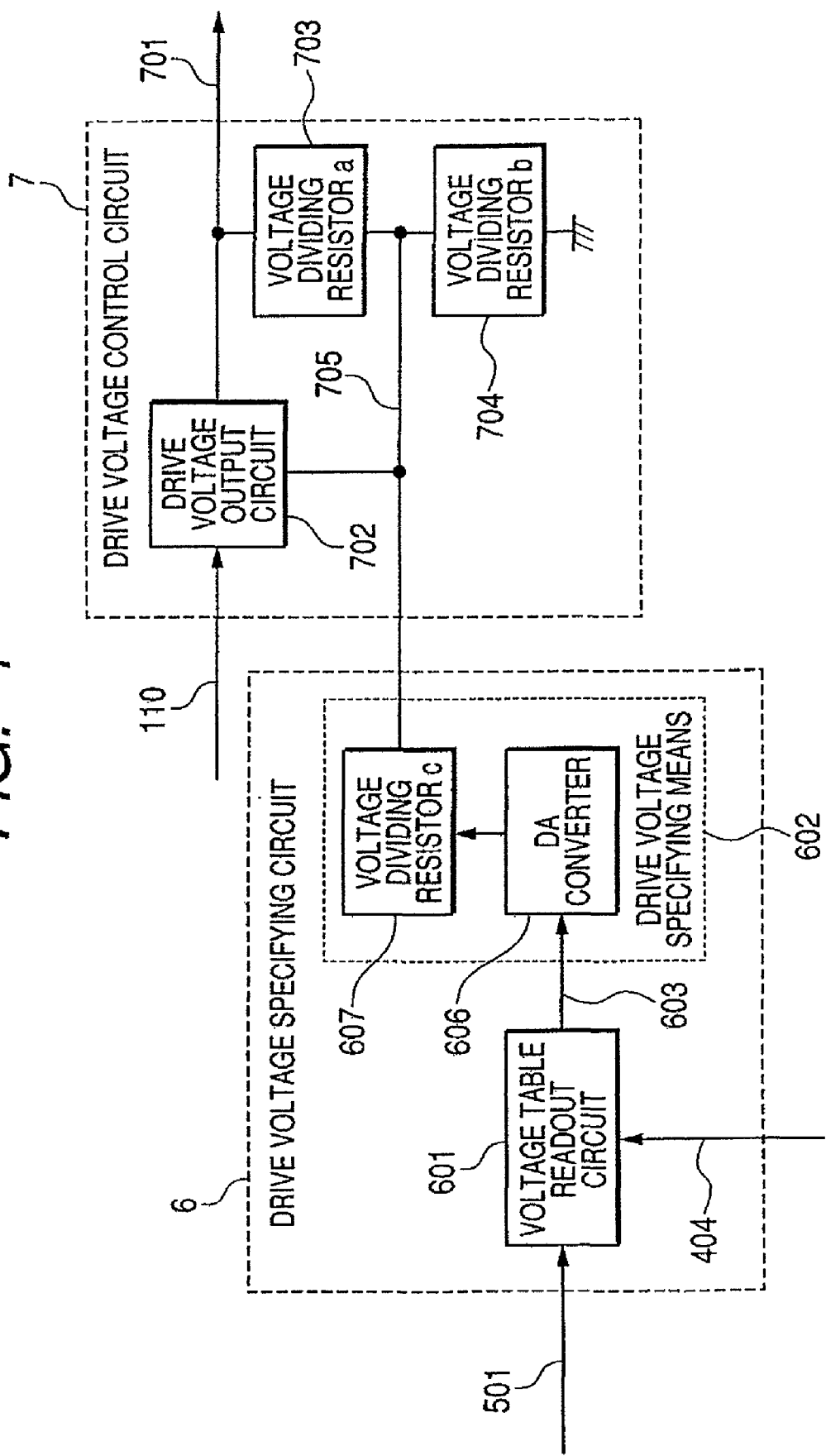
FIG. 4 is a circuit configuration diagram for explaining another example of voltage specifying means.

FIG. 4 is a circuit configuration diagram for explaining an example of another embodiment of the voltage specifying means 602 of the drive voltage specifying circuit 6. In FIG. 4, reference numeral 606 denotes a DA converter, and 607 denotes a voltage dividing resistor c. Output of the DA converter 606 is connected via the voltage dividing resistor c 607 to the feedback voltage 705 of the drive voltage control circuit 7 as a drive voltage specifying signal 604. This configuration also enables adjusting of the drive voltage 701 by changing the voltage ratio of the drive voltage 701 and the feedback voltage 705.

As shown in FIG. 4, this example also has a structure for taking the feedback voltage from a voltage dividing point obtained by resistance-dividing between a drive voltage and a reference voltage (typically, GND) to perform voltage adjustment. Such a configuration is also suitable for an inhaler. This is because the addition of relatively simple components such as a DA converter and a resistor to a generally used direct current power supply output circuit enables control of a drive voltage to a specified value during output of the drive voltage.

Second Embodiment

Figure 5:
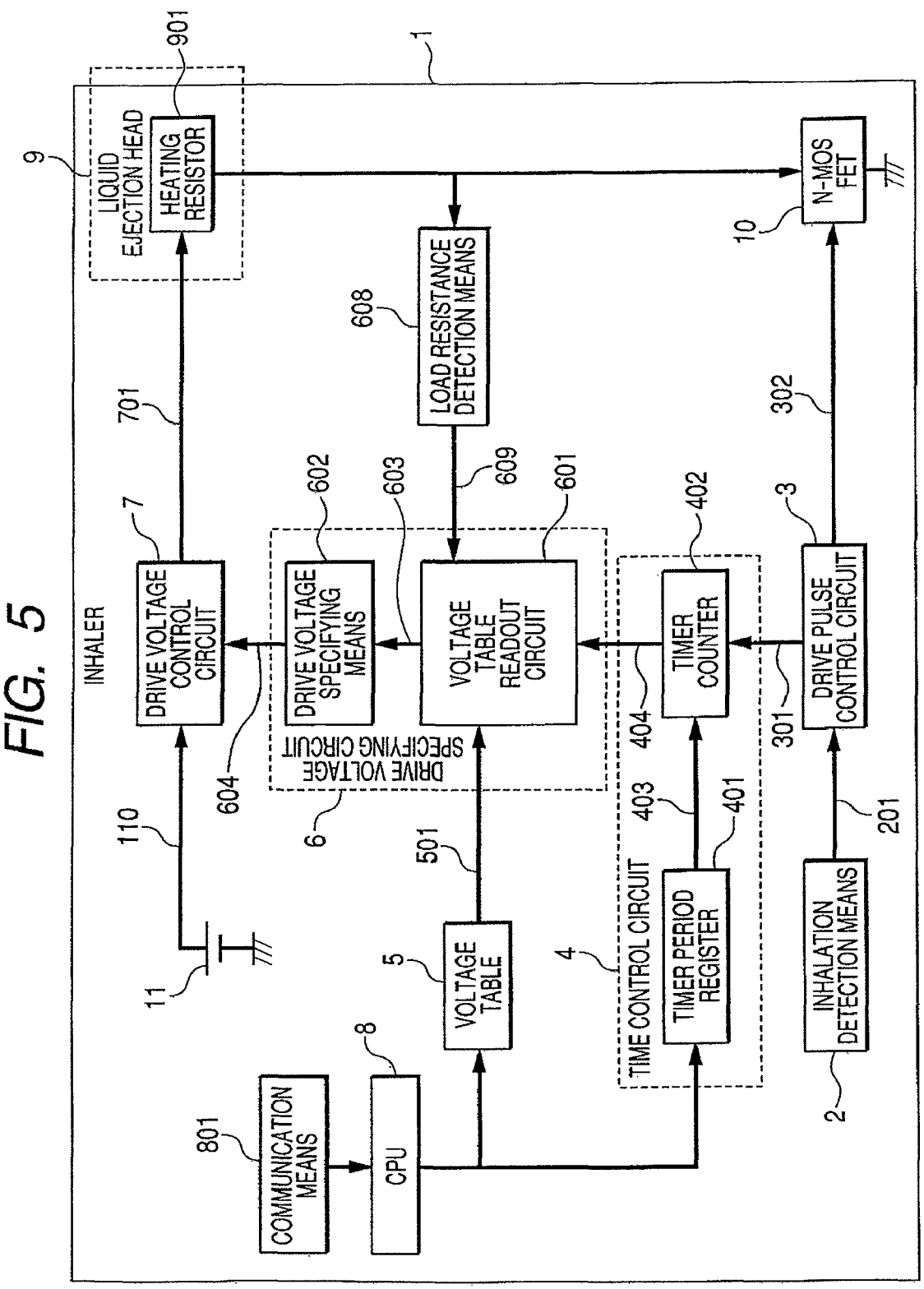
FIG. 5 is a circuit configuration diagram for explaining a second embodiment with load resistance detection means added thereto.

A second embodiment will now be described. FIG. 5 is a circuit configuration diagram for explaining a second embodiment in which load resistance detection means for detecting the resistance values of a heating resistor of a liquid ejection head was further added. In FIG. 5, a negative voltage terminal of a heating resistor 901 inside a liquid ejection head 9 is also connected to the load resistance detection means 608. Before the drive start, the load resistance detection means 608 detects a resistance value of the heating resistor 901. The resistance value of the heating resistor 901 that is detected by the load resistance detection means 608 is given to a voltage table readout circuit 601 as load resistance value information 609. The control of a voltage table 5 can be switched according to this information to perform voltage control. In this case, the voltage table 5 and voltage data 501 prepare regions and data for the number of switching performed prior to the drive start based on the resistance value of the heating resistor. Other points are the same as in the first embodiment. Thus, even in the second embodiment, preset voltage is sequentially specified from drive start for each similarly preset period (time interval), and under control of the drive voltage 701 based thereon, a current is applied to the heating resistor 901 according to a drive pulse signal 302, resulting in ejection of liquid droplets from the liquid ejection head 9.

According to the present embodiment, a liquid ejection head using a heating resistor has the following advantages. Since the existence of errors in resistance values due to production conditions is a known fact, control of a drive voltage to be appropriate for a resistance value of the heating resistor can be performed by measuring the resistance value prior to drive start. In this way, by having load resistance detection means for detecting the resistance values of the heating resistor of the liquid ejection head, the drive voltage specifying circuit becomes capable of switching the voltage table to be referred to according to the resistance value of the heating resistor.

Third Embodiment

Figure 6:
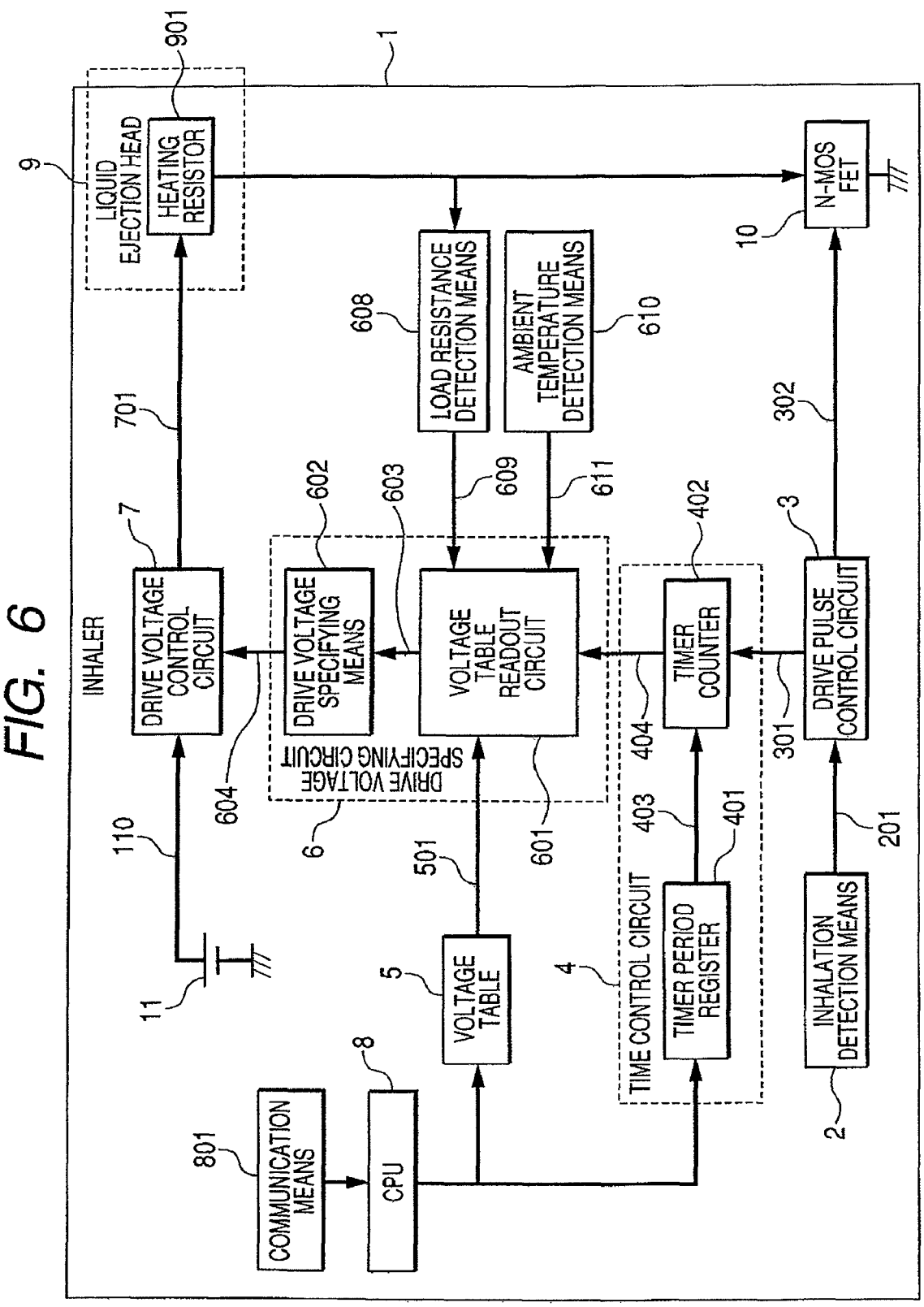
FIG. 6 is a circuit configuration diagram for explaining a third embodiment with ambient temperature detection means added thereto.

FIG. 6 is a circuit configuration diagram explaining a third embodiment in which ambient temperature detection means further was added. In FIG. 6, the ambient temperature detection means 610 detects the ambient temperature of an inhaler 1. The ambient temperature obtained by the ambient temperature detection means 610 is added to load resistance value information 609 and then given to a voltage table readout circuit 601 as ambient temperature value information 611. Control of a voltage table 5 may also be switched based on this information to perform the voltage control. In this case, the voltage table 5 and the voltage data 501 prepare regions and data for the number of switching performed prior to the drive start. Other points are the same as in the first embodiment.

According to the present embodiment, the following advantages may be achieved. Since ambient temperature of the inhaler does not remain constant during use by the user, ejection of liquid droplets will be influenced by ambient temperature in the case where the ejection utilizes bubbling due to the heating of the heating resistor. Therefore, the drive voltage can be controlled taking account of influences from ambient temperature by measuring the ambient temperature prior to the drive start.

In the above embodiment, while the voltage table 5 itself may be a rewritable non-volatile memory, a RAM may also be used. In this case, voltage data 501 is retained on a program memory for storing operation programs of a CPU 8 using a separately prepared rewritable non-volatile memory. Upon activation, the voltage data will be used after transferring it to the voltage table 5 that is composed of the RAM by the CPU 8. Additionally, in this case, the voltage data 501 that is rewritten via communication means 801 is data existing on either the program memory or the RAM.

When the voltage table is composed of a rewritable non-volatile memory, voltage data can be set from an external device, and the set voltage data can be retained even after cutting off the main power of the device. Moreover, such setting can be respectively performed on individual inhalers as well as according to characteristics of the liquid ejection heads that are used, and the setting can be retained even after cutting off the main power of the device.

Fourth Embodiment

Figure 7:
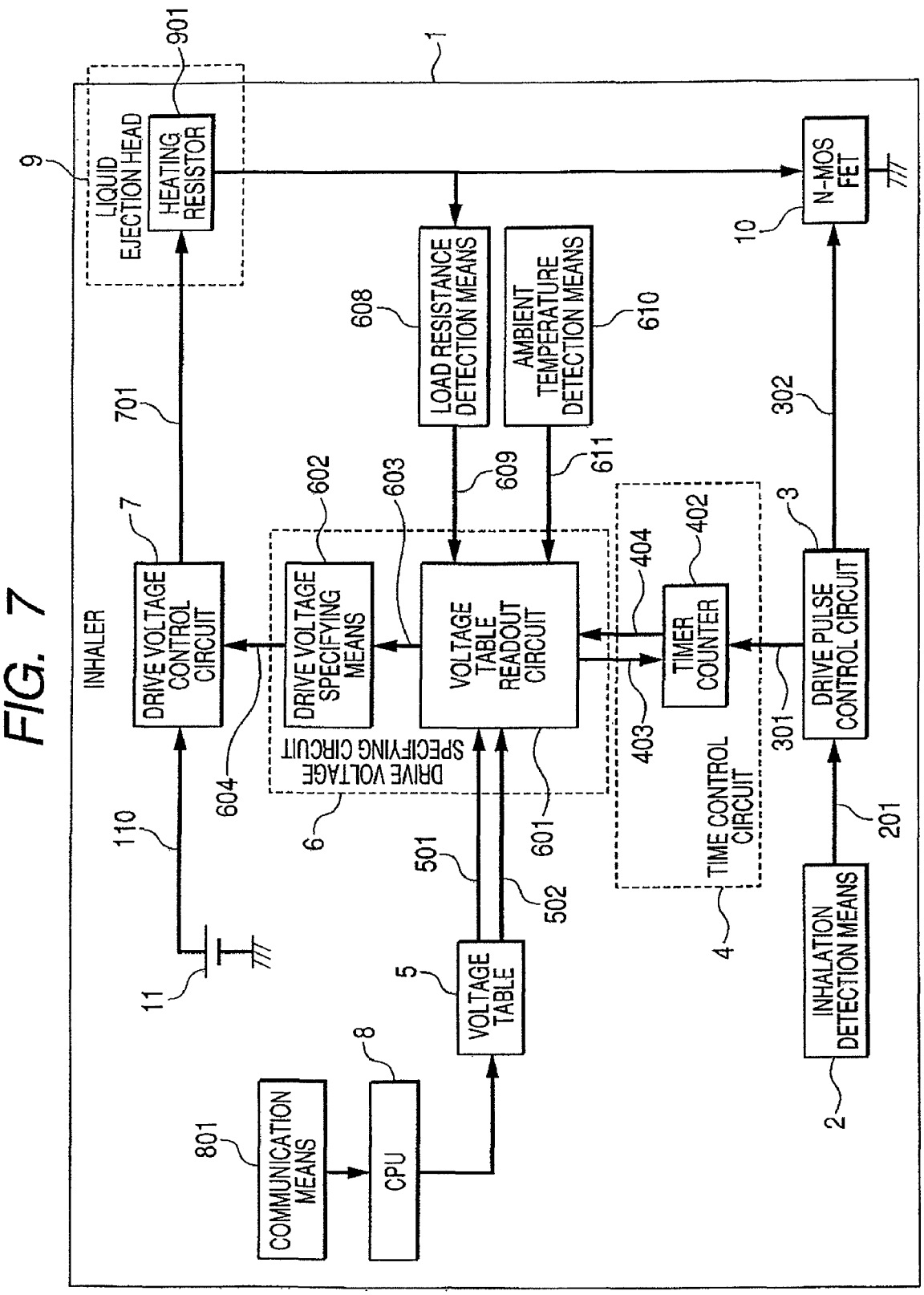
FIG. 7 is a circuit configuration diagram for explaining a fourth embodiment including a time control circuit as a different embodiment.

FIG. 7 is a circuit configuration diagram for explaining a fourth embodiment using a different example of a time control circuit. In this case, time interval data 502 is stored in a voltage table 5 in the same way as voltage data 501, and upon readout from the voltage data of the voltage table 5, the time interval data 502 is read together with the voltage data 501. Then, by using the time interval data 502 as period setting data 403, time intervals for specifying the next voltage can be specified differently for very time of specifying the voltage.

Fifth Embodiment

Although the inhaler has means for changing the drive voltage of a liquid ejection head with elapse of its drive time has been described in detail in the abovementioned embodiments 1 to 4, this means can also be changed to means for changing the drive period and/or drive pulse widths of a liquid ejection head with elapse of the drive time.

Figure 9:
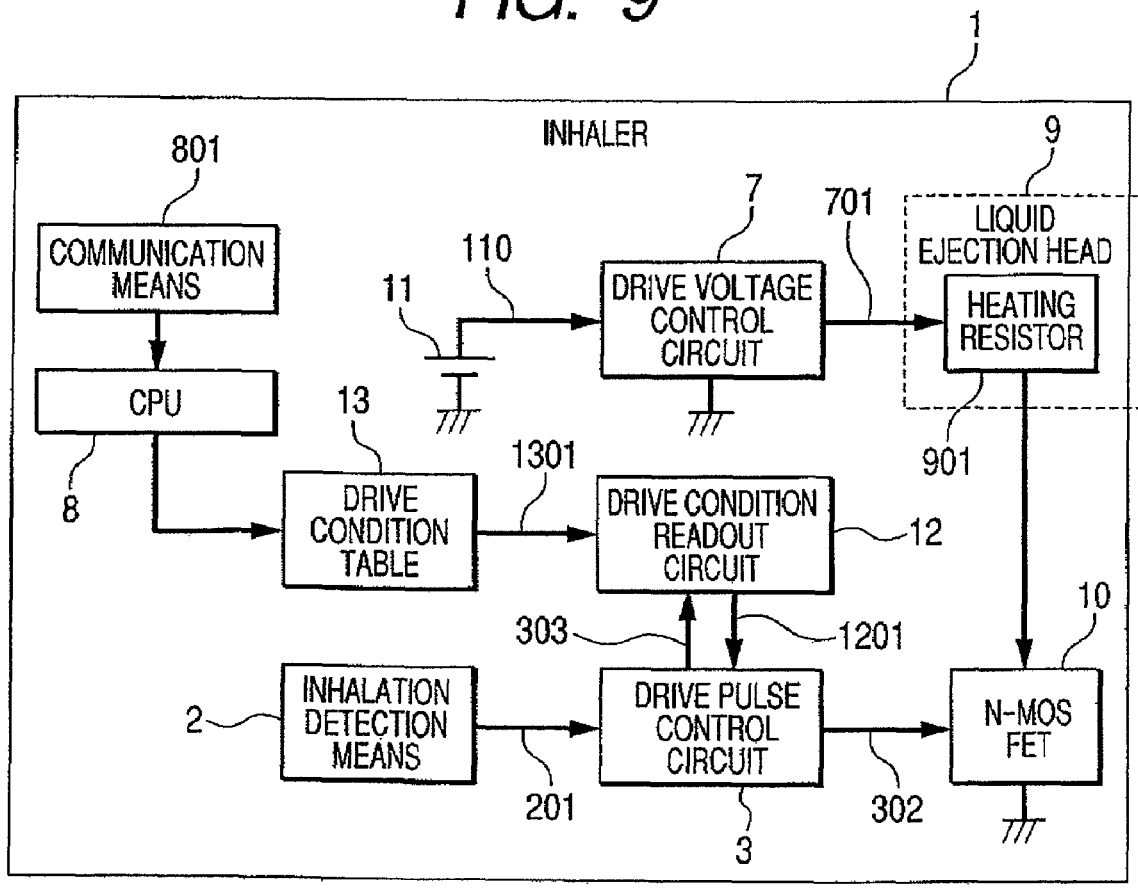
FIG. 9 is a circuit configuration diagram of an inhaler according to a fifth embodiment of the present invention.

As a fifth embodiment of the present invention, a specific example of a configuration wherein the switching means is also means for changing the drive periods of a liquid ejection head with elapse of its drive time will be described with reference to the drawing. FIG. 9 is a circuit configuration diagram of an inhaler of the present embodiment. In FIG. 9, reference numeral 12 denotes a drive condition readout circuit, while 13 denotes a drive condition table.

In the above configuration, when inhalation detection means 2 detects inhalation by a user via a mouthpiece 102, the inhalation detection means 2 notifies a drive pulse control circuit 3 using an inhalation detection signal 201, and instructs drive start.

Upon receiving instructions for the drive start, the drive pulse control circuit 3 requests drive conditions from a drive condition readout circuit 12 using a drive condition request signal 303. Incidentally, the drive condition request signal 303 is a signal with a logical level that becomes true when a new drive condition is required, and remains true until the new drive condition is set.

For each drive condition request signal 303, the drive condition readout circuit 12 sequentially reads out drive condition data 1301 from a drive condition table 13, and sets drive conditions at the drive pulse control circuit 3 using drive condition setting signals 1201.

After a drive condition is set by the drive condition setting signal 1201, the drive pulse control circuit 3 withdraws the drive condition request signal 303, and controls drive pulse signals 302 according to the set drive condition to perform the liquid ejection of the liquid ejection head 9.

Drive conditions to be set at the drive pulse control circuit 3 include ON period condition and OFF period condition of the drive pulse signal 302, number of ON/OFF repetitions, and a continuation/termination flag. The drive pulse control circuit 3 performs switching ON/OFF of the drive pulse signal 302 during the set ON period and OFF period for the number of repetitions. When the continuation/termination flag indicates continuation after control of the drive pulse signal 302 for the set number of repetitions is completed, a new drive condition request is made to the drive condition readout circuit using a drive condition request signal 303. When the continuation/termination flag indicates termination, ejection control is terminated without making new requests.

INDUSTRIAL APPLICABILITY

In addition to the above-described inhaler, the present invention may be used as a direct current power supply control device that controls a voltage from a general direct current power supply to output to a drive object in any application where such voltage control is required.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2005-129059 filed Apr. 27, 2005, which is hereby incorporated by reference herein.

The invention claimed is:

1. An inhaler for use in a user's inhalation of a liquid, comprising:
   a liquid ejection head for ejecting a liquid; and
   a drive unit for reading a voltage data from a plurality of preset voltage data respectively corresponding to preset time intervals, and driving said liquid ejection head at a drive voltage specified based on the read voltage data,
   wherein said drive unit comprises:
      a drive pulse control circuit for controlling a drive pulse signal of the liquid ejection head;
      a voltage table for recording a drive voltage corresponding to each time interval as voltage data;
      a drive voltage specifying circuit for specifying the drive voltage by reading the voltage data from the voltage table;
      a time control circuit for instructing said drive voltage specifying circuit to read the voltage data from said voltage table corresponding to each time interval in synchronization with the drive pulse signal; and
      a drive voltage control circuit for outputting at the specified drive voltage to the liquid ejection head based on the drive pulse signal.

2. The inhaler according to claim 1, wherein said drive voltage control circuit has a structure that takes a feedback voltage from a voltage dividing point obtained by resistance-dividing a voltage between a drive voltage and a reference voltage to perform voltage adjustment.

3. The inhaler according to claim 1, wherein the plurality of preset of voltage data is specified on a basis of temperature rise characteristics of the liquid ejection head and temporal change characteristics of the drive voltage necessary for liquid ejection.

\* \* \* \* \*